(12) United States Patent
Fiorenza

(10) Patent No.: US 11,835,144 B2
(45) Date of Patent: Dec. 5, 2023

(54) VALVE FOR BYPASS CONDUIT

(71) Applicant: SMART RS INC., Ottawa (CA)

(72) Inventor: Francesco Fiorenza, Ottawa (CA)

( * ) Notice: Subject to any disclaimer, the term of this patent is extended or adjusted under 35 U.S.C. 154(b) by 0 days.

(21) Appl. No.: 17/869,564

(22) Filed: Jul. 20, 2022

(65) Prior Publication Data

US 2023/0028878 A1    Jan. 26, 2023

Related U.S. Application Data

(60) Provisional application No. 63/223,780, filed on Jul. 20, 2021.

(51) Int. Cl.
| | | |
|---|---|---|
| *F16K 15/03* | (2006.01) | |
| *F16K 1/20* | (2006.01) | |
| *F16K 11/052* | (2006.01) | |

(52) U.S. Cl.
CPC .......... *F16K 1/205* (2013.01); *F16K 11/052* (2013.01); *F16K 15/03* (2013.01)

(58) Field of Classification Search
CPC ...... F16K 22/044; F16K 22/052; F16K 15/03; F16K 15/031; F16K 15/034; F16K 27/0227
See application file for complete search history.

(56) References Cited

U.S. PATENT DOCUMENTS

| | | | | |
|---|---|---|---|---|
| 3,292,653 A * | 12/1966 | Scaramucci | ............ | F16K 15/03 137/516.29 |
| 3,610,698 A * | 10/1971 | Gachot | .................... | F16K 11/02 137/856 |
| 4,090,529 A * | 5/1978 | Schuller | .................. | F16K 15/03 137/527 |
| 4,191,205 A * | 3/1980 | Nash | ........................ | F16K 15/03 137/527.8 |
| 4,274,436 A * | 6/1981 | Smith | .................. | F16K 27/0227 137/527 |
| 6,394,136 B1 * | 5/2002 | Rohrbeck | .............. | F16K 11/052 137/867 |
| 6,397,874 B1 * | 6/2002 | Featheringill | ........... | F16K 15/03 137/205 |
| 7,082,944 B2 * | 8/2006 | Gossweiler | .............. | A62B 9/02 128/205.24 |
| 10,948,092 B2 * | 3/2021 | Fink | ......................... | F16K 15/03 |
| 2022/0381355 A1 * | 12/2022 | Raisanen | ................. | F16K 31/14 |

* cited by examiner

*Primary Examiner* — Hailey K. Do
(74) *Attorney, Agent, or Firm* — Andrews Robichaud PC; Alessandro Colonnier

(57) ABSTRACT

A valve for a bypass conduit is comprised of a rigid inner frame having an arm with a tab at one end and a hinge at an opposite end. A flexible outer seal is positioned over the inner frame, the flexible outer seal defining a peripheral edge to substantially house the tab and arm of the inner frame. The valve is pivotable from a first position to a second position on the bypass conduit.

15 Claims, 13 Drawing Sheets

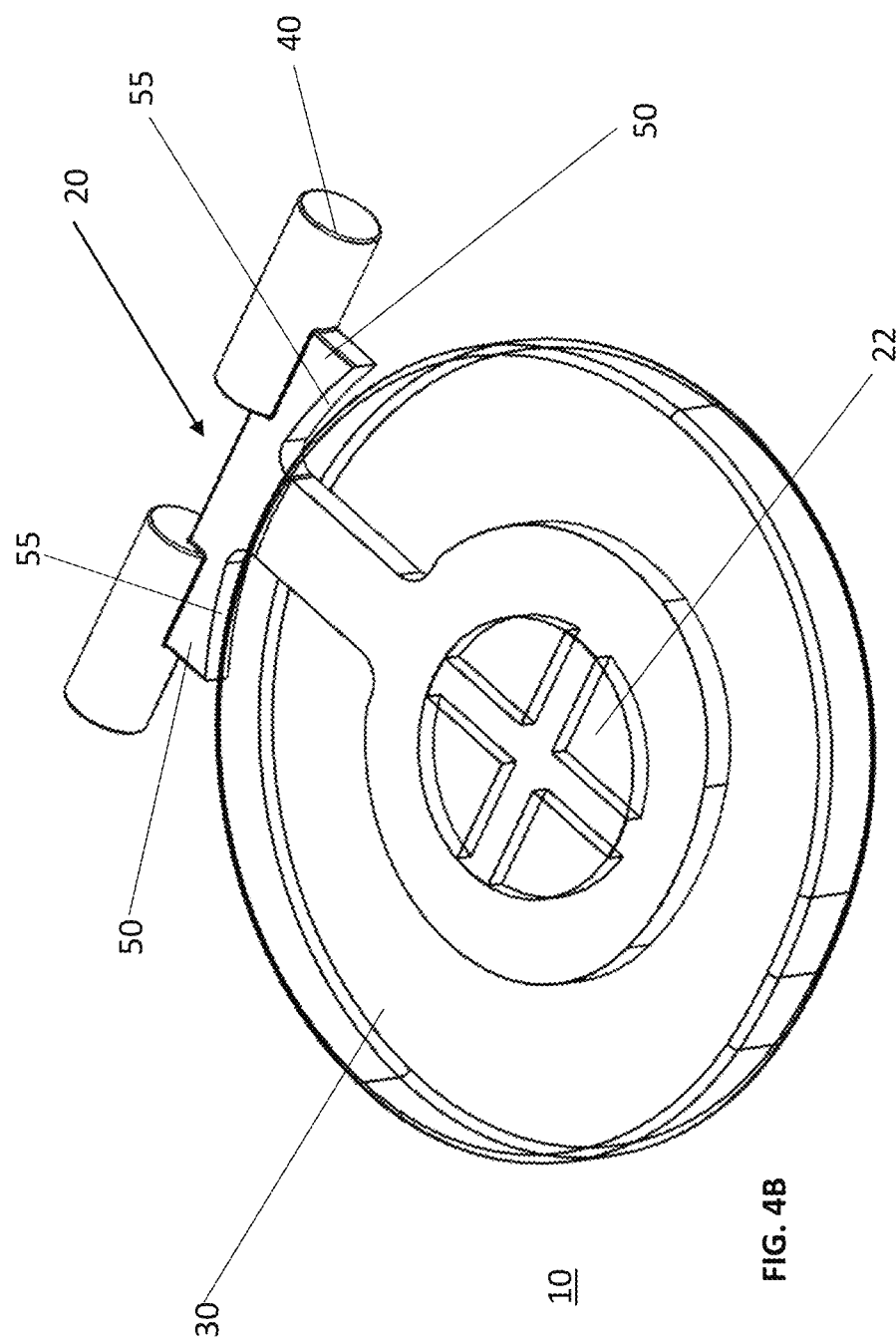

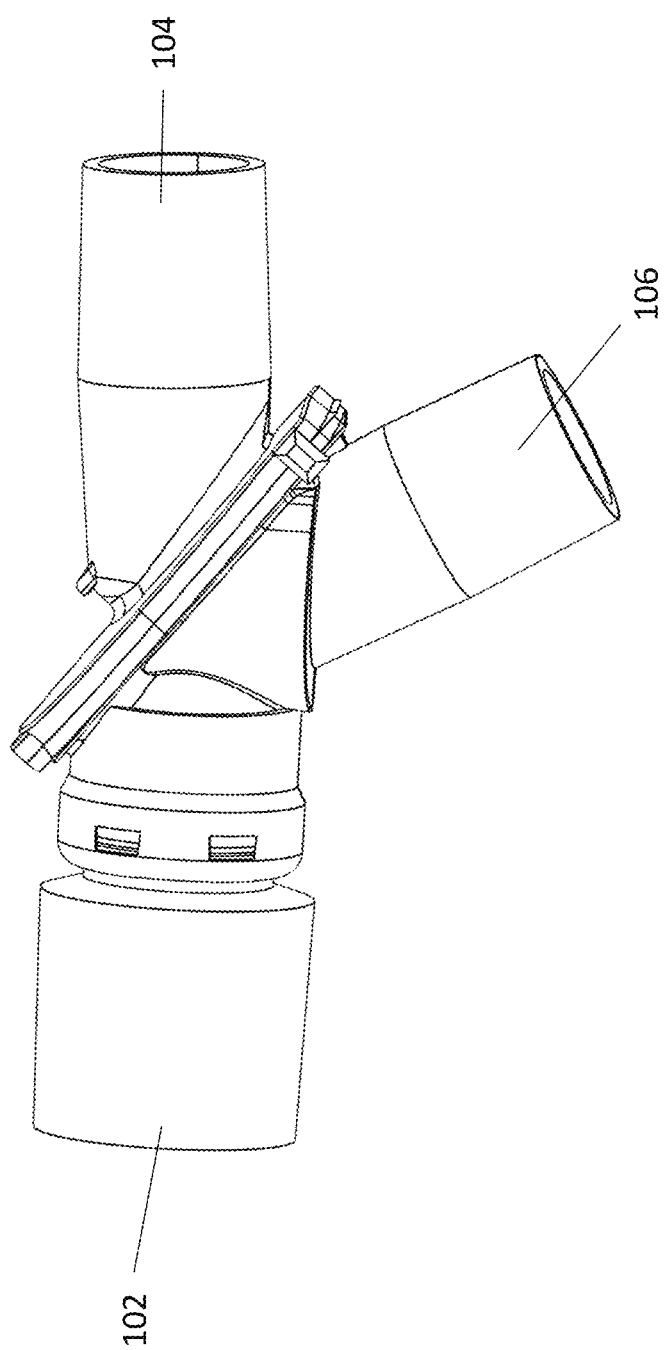

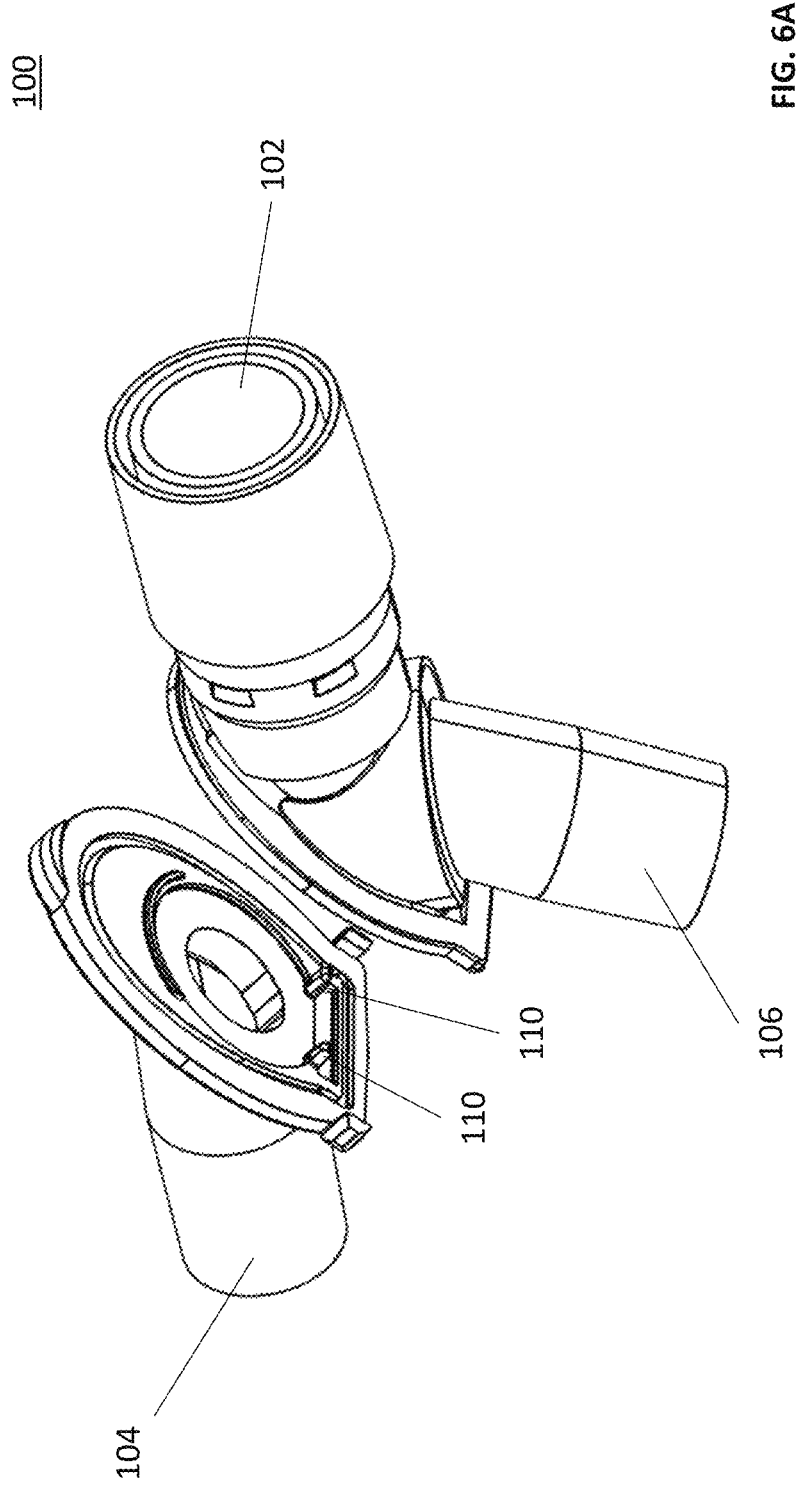

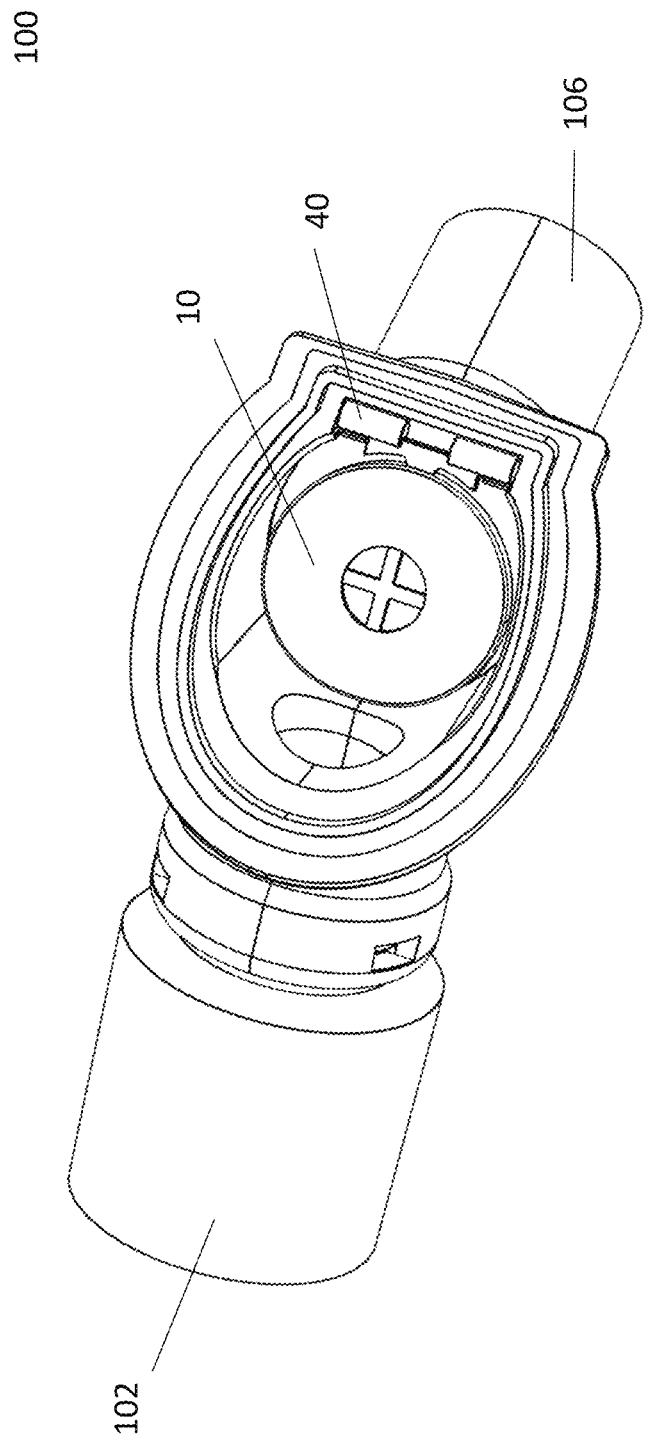

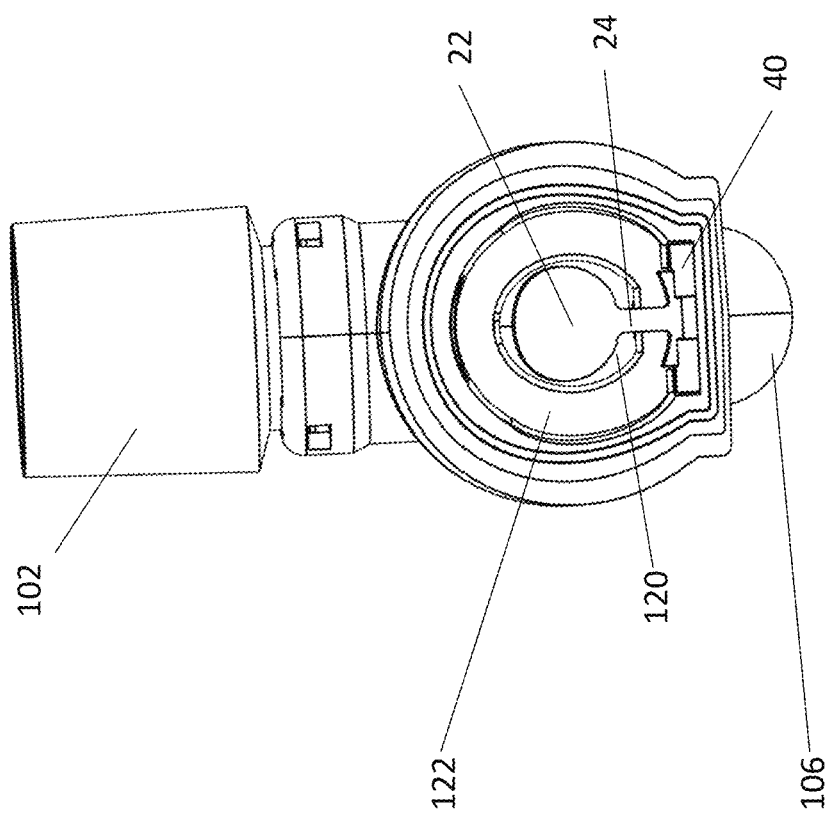

VALVE FOR BYPASS CONDUIT

FIELD

The invention relates to the field of bypass conduits, and more specifically to improved valves for respiratory bypass conduits.

BACKGROUND

Valves for bypass conduit have been prevalent in the market, such as those described in U.S. Pat. No. 11,079,026 (Fiorenza). Unfortunately, a limitation of the valve described in Fiorenza is that the central rigid member is U-shaped, which is difficult to assemble when the flexible outer member is slid on. Another drawback of the U-shaped rigid member is that it does not flex at all, such that when there is air pressure created in the bypass valve, the flexible outer member pulls inwardly or outwardly, which in turn pulls on the U-shaped rigid member and can unseal the valve within the bypass.

As such, there is a need for a new valve that has a central member that is rigid but slightly flexible, having a flexible outer member that can flex as well, but whose peripheral edges remain secured and sealed against the walls of the bypass conduit.

SUMMARY

In an aspect, the present disclosure provides a valve for a bypass conduit, the valve comprising: a rigid inner frame the rigid inner frame further comprising: a hinge configured to allow the valve to pivot; an arm member extending from the hinge, the arm member terminating in a tab member; and, a flexible outer seal positioned over the rigid inner frame, the flexible outer seal defining a peripheral edge to substantially house the tab member and arm member of the inner frame, wherein the valve is movable from a first position to a second position on the bypass conduit.

BRIEF DESCRIPTION OF THE DRAWINGS

The following figures serve to illustrate various embodiments of features of the disclosure. These figures are illustrative and are not intended to be limiting.

FIG. 4B is a perspective transparent view of the flexible seal positioned over the inner frame of the valve, according to an embodiment of the present disclosure;

FIG. 5 is a side view of a valve conduit which can house a valve according to an embodiment of the present disclosure;

FIG. 6A is a side perspective view of a valve conduit having a valve of the present invention with a port displaced from the valve conduit according to an embodiment of the present disclosure;

FIG. 7 is a top view of a valve conduit having a valve installed within the valve conduit according to an embodiment of the present disclosure;

FIG. 8A is a top view of a valve conduit having a valve without the outer seal within the valve conduit according to an embodiment of the present disclosure;

DETAILED DESCRIPTION

The following embodiments are merely illustrative and are not intended to be limiting. It will be appreciated that various modifications and/or alterations to the embodiments described herein may be made without departing from the disclosure and any modifications and/or alterations are within the scope of the contemplated disclosure.

Figure 1:
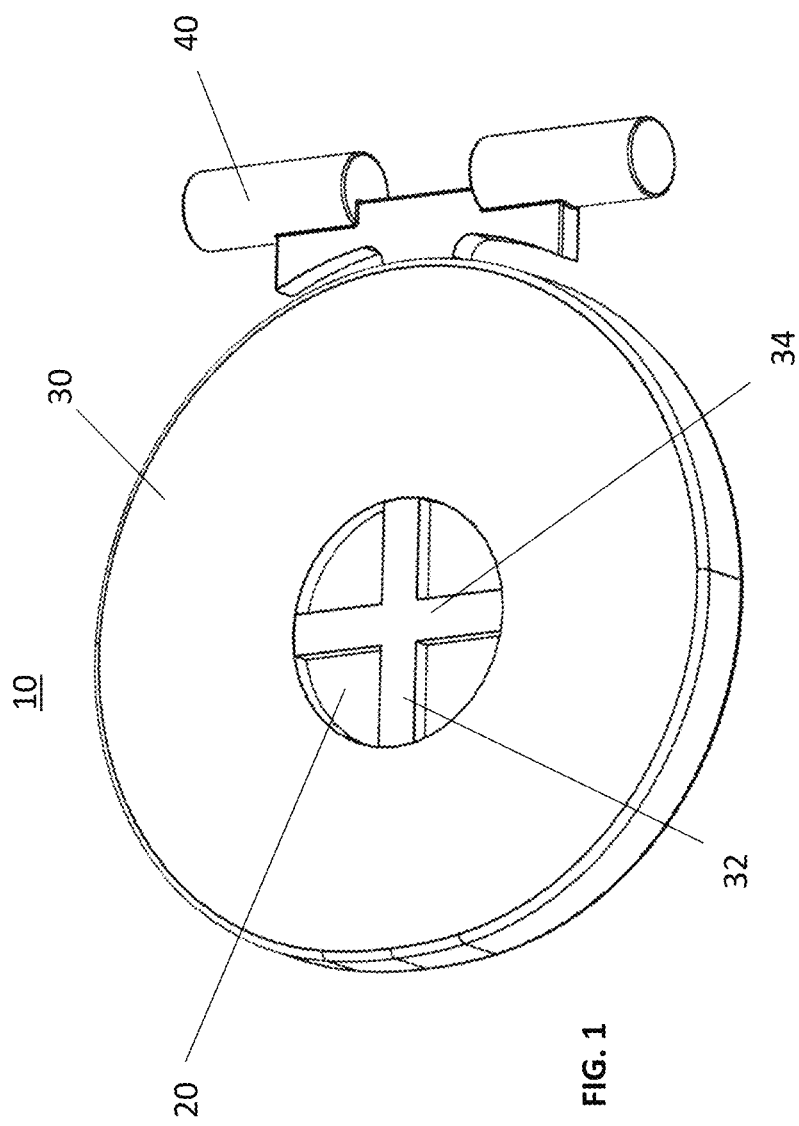
FIG. 1 is a perspective view of a valve according to an embodiment of the present disclosure.
Figure 2:
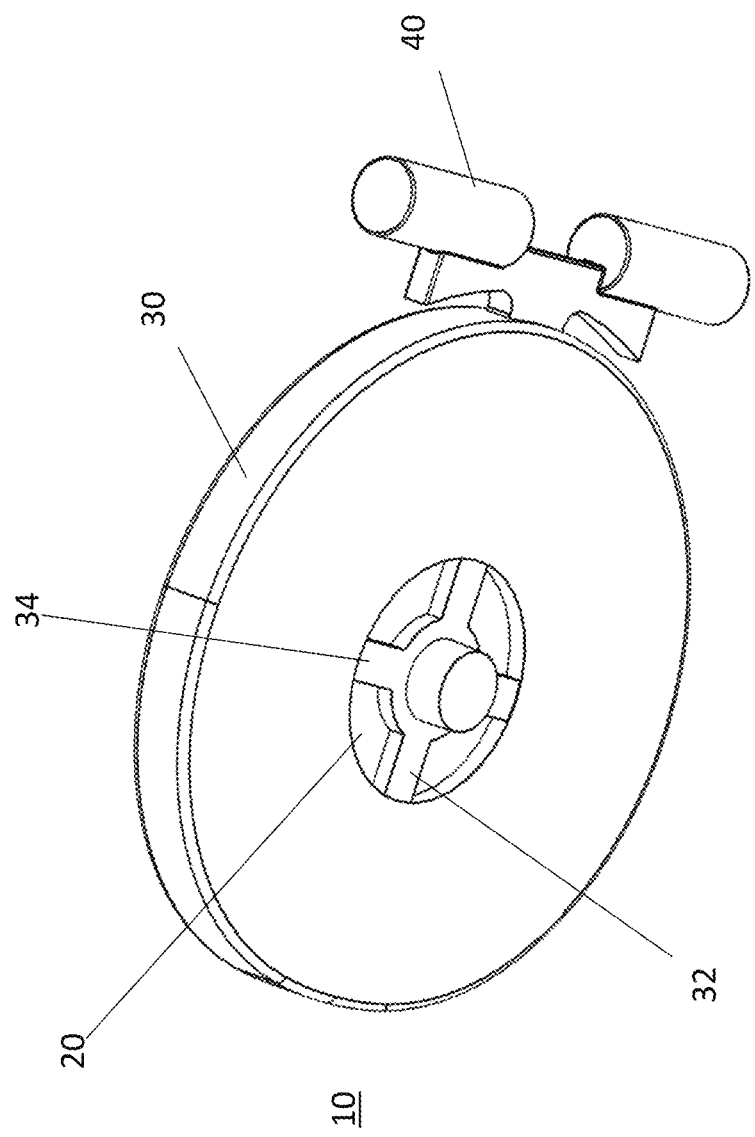
FIG. 2 is a perspective view of the underside of a valve according to one embodiment of the present disclosure.
Figure 3:
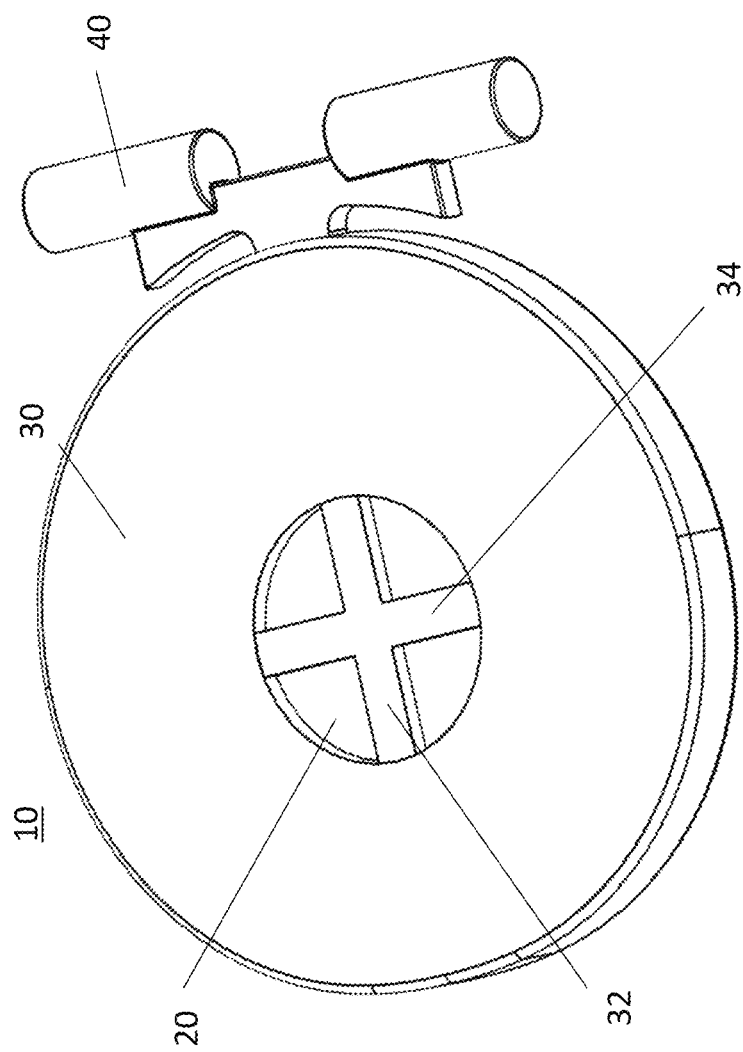
FIG. 3 is another perspective view of a valve according to an embodiment of the present disclosure.

With reference to FIGS. 1, 2 and 3 and according to an embodiment of the present disclosure, a valve 10 for use in a respiratory bypass conduit (not shown) is disclosed. The valve 10 is comprised of a rigid inner frame 20 that provides rigidity to a flexible outer seal 30. The inner frame 20 is defined by a flap member 22 and an arm 24 connected to a hinge 40 at the opposite end. The hinge 40 is designed to mate with a corresponding slot (not shown) of the bypass conduit (not shown) to move the valve 10 from a first position to a second position. The first position is the area where the valve 10 covers an aperture in a first portion of the valve conduit (not shown), and the second position is the area where the valve 10 covers another aperture in a second portion of the valve conduit (not shown).

With further reference to FIGS. 1, 2 and 3 and according to one embodiment of the present invention, the flexible outer seal 30 has cross-members 32 and 34 that allow to further secure outer seal 30 onto inner frame 20, as opposed to having an opening without any cross-members. Cross-members 32 and 34 reduce the possibility of outer seal 30 peeling away from inner frame 20. The flexible outer seal 30 can be made of any suitable materials that is pliable allowing for a seal and acceptable for medical applications.

Figure 4A:
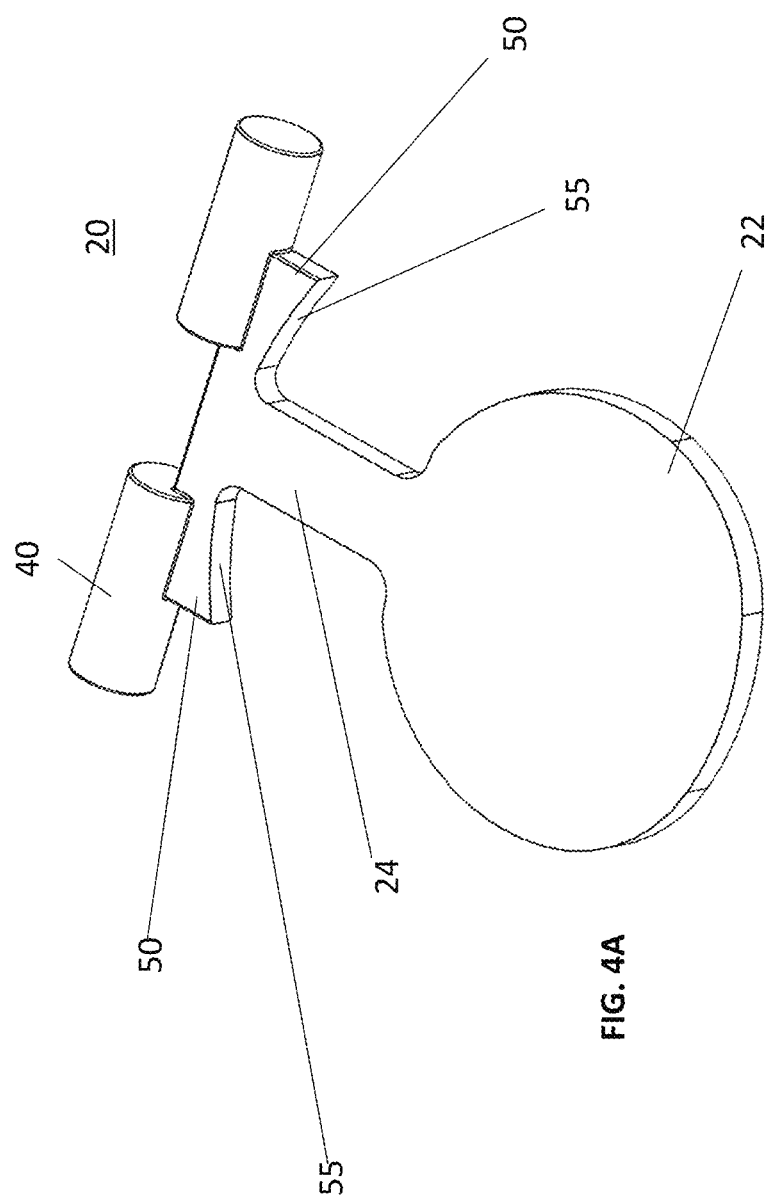
FIG. 4A is a perspective view of the inner frame of a valve according to an embodiment of the present disclosure.

With reference to FIGS. 4A and 4B and according to one embodiment of the present invention, inner frame 20 has a tab and an arm 24 connected to hinge 40 allowing for the movement of the valve in a first and second position within a bypass conduit (not shown). The circular shape of the tab 22 generally corresponds to the circular shape of the flexible seal 30. Indeed, the flexible seal 30 is moulded over the tab 22 and the arm 24. The inner frame 20 is further comprised of two guiding flanges 50 that make contact with an inner portion (not shown) of a conduit (not shown) to keep the valve 10 aligned and moving between the first and second positions. Indeed, the guiding flanges 50 create the requisite friction to maintain the correct pivoting of the valve 10. Each one of the guiding flanges 50 is comprised of a sloping inner surface 55 to reduce the weight of the inner frame 20, and also mate more flushly with the correspondingly circular peripheral edge of the flexible seal 30.

Figure 6B:
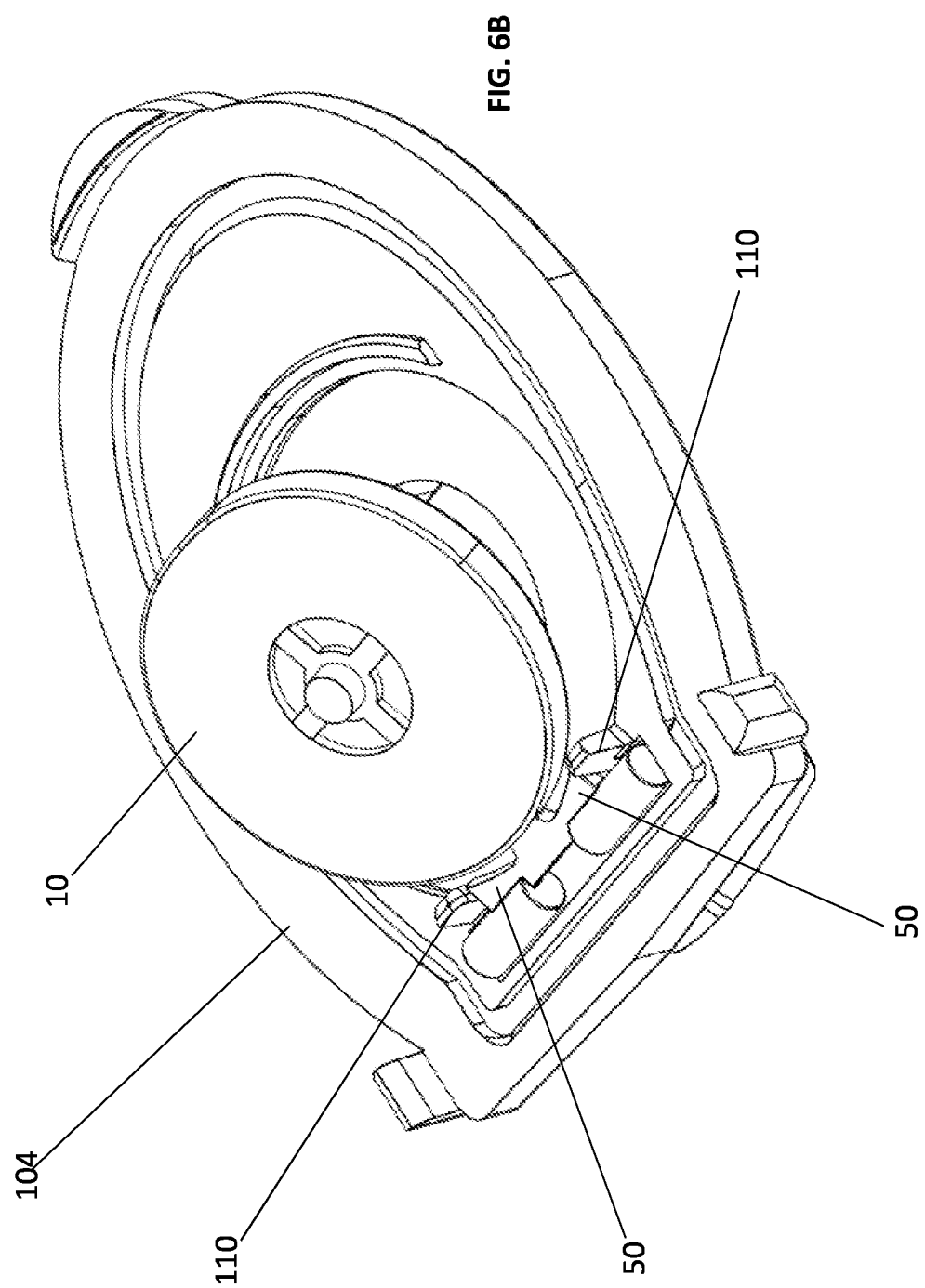
FIG. 6B is an enlarged perspective view of the valve pivotable within a port, according to an embodiment of the present disclosure.

With reference to FIGS. 5, 6A and 6B and according to one embodiment of the present invention, a valve conduit 100 having a valve 10 is shown. Valve conduit 100 has ports 102, 104 and 106 wherein a valve of the present invention will close either port 104 or 106. With specific reference to FIGS. 6A and 6B and according to one embodiment of the present invention, port 104 is removed from valve conduit 100 showing guiding protrusions 110 for the valve 10. The guiding flanges 50 make contact with the guiding protrusions 110 and slide along such guiding protrusions 110 during the pivoting of the valve 10. In other words, the guiding protrusions 110 prevent any lateral movement of the valve 10 during movement from the first to the second position.

With reference to FIG. 7 and according to one embodiment of the present invention, a valve conduit 100 having valve 10 positioned within an aperture of port 106. As shown, the aperture (not shown) being closed is completely sealed by valve 10, which ensures that air will pass wholly from port 102 to port 104 (not shown) or vice versa. In other words, no air will go through port 106.

With further reference to FIG. 7 and according to one embodiment of the present invention, the hinge portion 40 of the valve 10 consists of two cylindrical members allowing for the valve 10 to pivot as further described below. A worker skilled in the relevant art would be familiar with other shapes for these cylindrical members allowing the valve 10 to pivot.

Figure 8B:
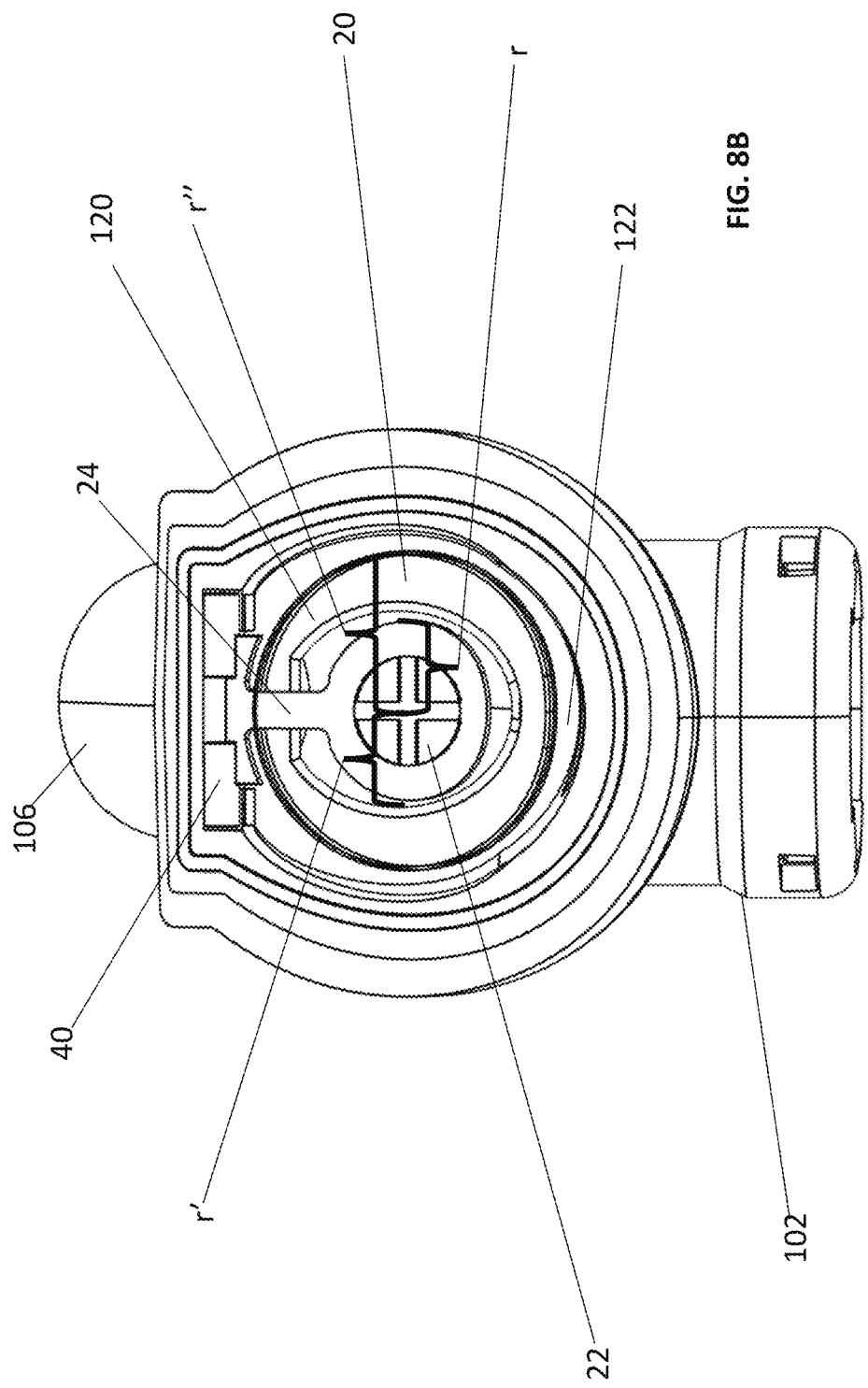
FIG. 8B is an enlarged top view of a valve conduit having a valve with the outer seal shown transparently, according to an embodiment of the present disclosure.
Figure 8C:
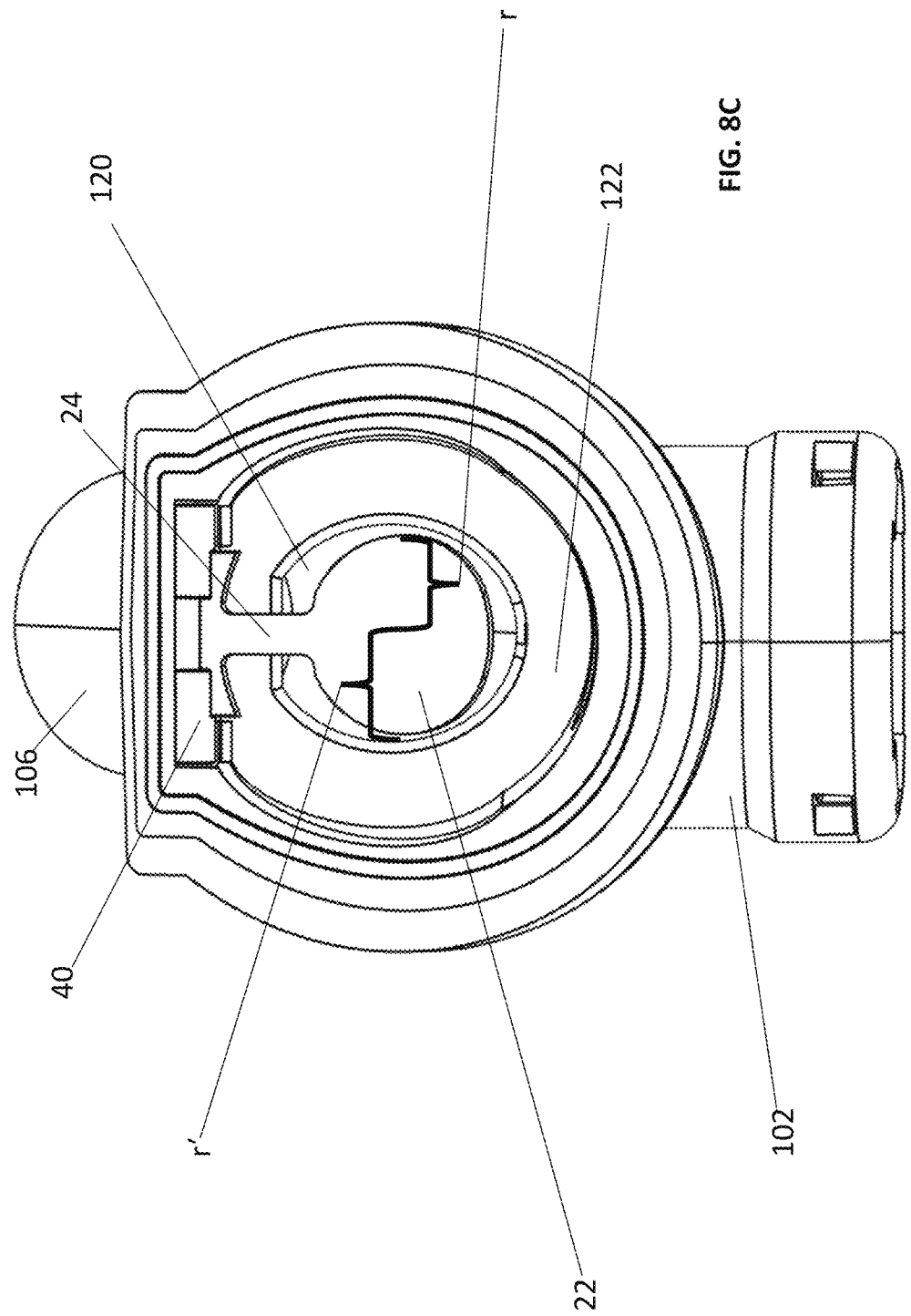
FIG. 8C is am enlarged top view of a valve conduit having a valve without the outer seal, according to an embodiment of the present disclosure.

With reference to FIGS. 8A, 8B and 8C and according to one embodiment of the present invention, the valve conduit 100 is shown having a valve 10 of the present invention without an outer seal (not shown). Tab 22 and arm 24 of inner frame 20 are positioned over aperture 120 of port 106. Tab 22 has a shape that is slightly smaller than aperture 120, which is a key feature of the present invention. Specifically, by having tab 22 smaller than aperture 120 allows for arm 24 to flex when air pressure is present within the valve 10. Arm 24 will flex, allowing tab 22 to move slightly inwardly within aperture 120 while the flexible outer seal (not shown), whose peripheral edges will remain connected and sealed to the outer wall 122 of the aperture 120, ensures optimal closure of aperture 106. In a preferred embodiment as best shown in FIGS. 8B and 8C, the tab 22 has a first radius r, the aperture 120 has a second radius r', and the flexible seal 20 has a third radius r'', whereby the relationship between radii is defined as:

$$r > r' > r''$$

Figure 9:
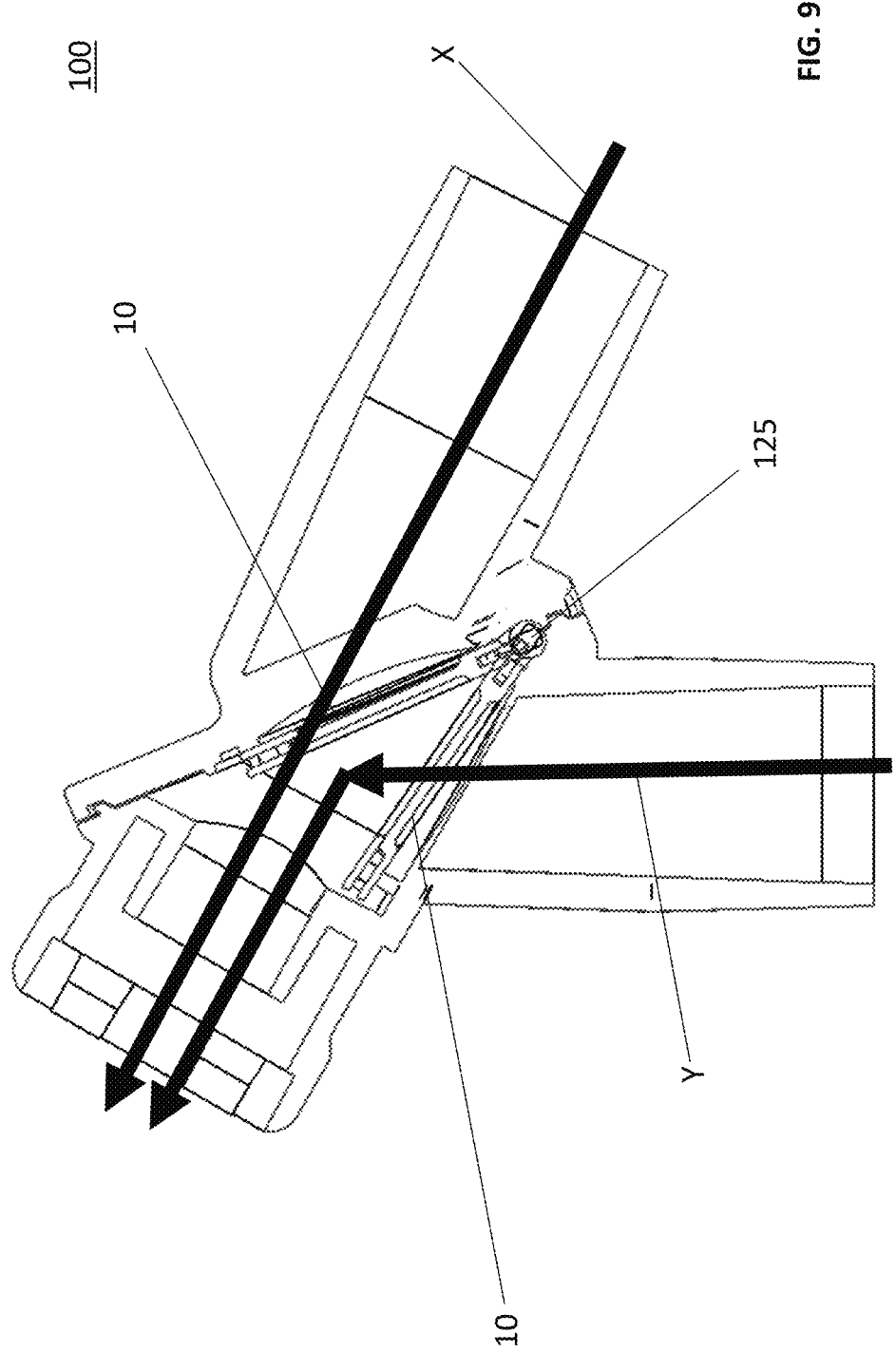
FIG. 9 is an air flow diagram with a valve in either a first or second position within a valve conduit according to an embodiment of the present disclosure.

With reference to FIG. 9 and according to an embodiment of the present disclosure, the valve 10 is shown positioned in a bypass conduit 100. Indeed, the hinge 40 of the valve 10 is secured into the slot 125 of the bypass conduit 100. The valve 10 is shown moving from a first position to a second position within the bypass conduit 100. A worker skilled in the art would appreciate that when the valve 10 is in the first position, air can flow through the bypass conduit 100 in direction X, while when the valve is in the second position, air can flow through the bypass conduit in direction Y.

Many modifications of the embodiments described herein as well as other embodiments may be evident to a person skilled in the art having the benefit of the teachings presented in the foregoing description and associated drawings. It is understood that these modifications and additional embodiments are captured within the scope of the contemplated disclosure which is not to be limited to the specific embodiment disclosed.

The invention claimed is:

1. A valve for a bypass conduit, the valve comprising:
a rigid inner frame, the rigid inner frame further comprising:
  a hinge configured to allow the valve to pivot;
  an arm member extending from the hinge, the arm member terminating in a tab member; and,
a flexible outer seal positioned over the rigid inner frame, the flexible outer seal defining a peripheral edge to substantially house the tab member and arm member of the inner frame, the flexible outer seal comprising at least one cross-member to improve adherence of the flexible outer seal onto the rigid inner frame,
wherein the valve is movable from a first position to a second position on the bypass conduit.

2. The valve of claim 1 wherein the tab member has a circular shape.

3. The valve of claim 1 wherein the tab member has a first radius X, the flexible outer seal has a second radius Y, and the bypass conduit has ports having openings with third radius Z, whereby X>Z>Y.

4. The valve of claim 1 further comprised of two guiding flanges positioned in between the hinge and the arm member, the two guiding flanges cooperating with two guiding protrusions of the bypass conduit to eliminate lateral movement of the valve within the bypass conduit.

5. The valve of claim 4 wherein each one of the two guiding flanges are comprised of a sloping inner surface to reduce the weight of the rigid inner frame and better mate with the peripheral edge of the flexible outer seal.

6. A valve for a bypass conduit, the valve comprising:
a rigid inner frame, the rigid inner frame further comprising:
  a hinge configured to allow the valve to pivot;
  an arm member extending from the hinge, the arm member terminating in a tab member;
a flexible outer seal positioned over the rigid inner frame, the flexible outer seal defining a peripheral edge to substantially house the tab member and arm member of the inner frame; and,
two guiding flanges positioned in between the hinge and the arm member, the two guiding flanges cooperating with two guiding protrusions of the bypass conduit to eliminate lateral movement of the valve within the bypass conduit,
wherein the valve is movable from a first position to a second position on the bypass conduit.

7. The valve of claim 6 wherein the flexible outer seal is further comprised of at least one cross-member to improve adherence of the flexible outer seal onto the rigid inner frame.

8. The valve of claim 6 wherein each one of the two guiding flanges are comprised of a sloping inner surface to reduce the weight of the rigid inner frame and better mate with the peripheral edge of the flexible outer seal.

9. The valve of claim 6 wherein the tab member has a circular shape.

10. The valve of claim 6 wherein the tab member has a first radius X, the flexible outer seal has a second radius Y, and the bypass conduit has ports having openings with third radius Z, whereby X>Z>Y.

11. A valve for a bypass conduit, the valve comprising:
a rigid inner frame, the rigid inner frame further comprising:
  a hinge configured to allow the valve to pivot;
  an arm member extending from the hinge, the arm member terminating in a tab member;
a flexible outer seal positioned over the rigid inner frame, the flexible outer seal defining a peripheral edge to substantially house the tab member and arm member of the inner frame; and, two guiding flanges positioned in between the hinge and the arm member, the two guiding flanges cooperating with two guiding protrusions of the bypass conduit to eliminate lateral movement of the valve within the bypass conduit, wherein the valve is movable from a first position to a second position on the bypass conduit, and wherein the tab member has a first radius X, the flexible outer seal has a second radius Y, and the bypass conduit has ports having openings with third radius Z, whereby X>Z>Y.

12. The valve of claim 11 wherein the flexible outer seal is further comprised of at least one cross-member to improve adherence of the flexible outer seal onto the rigid inner frame.

13. The valve of claim 11 further comprised of two guiding flanges positioned in between the hinge and the arm member, the two guiding flanges cooperating with two guiding protrusions of the bypass conduit to eliminate lateral movement of the valve within the bypass conduit.

14. The valve of claim 11 wherein each one of the two guiding flanges are comprised of a sloping inner surface to reduce the weight of the rigid inner frame and better mate with the peripheral edge of the flexible outer seal.

15. The valve of claim 11 wherein the tab member has a circular shape.

* * * * *